(12) United States Patent
Ghannam et al.

(10) Patent No.: US 11,433,072 B1
(45) Date of Patent: Sep. 6, 2022

(54) ORAL DOSAGE FORMS OF IBRUTINIB

(71) Applicant: Hikma Pharmaceuticals USA Inc., Berkeley Heights, NJ (US)

(72) Inventors: Mahmoud Ghannam, Amman (JO); Shahin Fesharaki, Weston, FL (US); Mohammad Al Hreebat, Amman (JO); Ahmad Arif Mohammad, Amman (JO)

(73) Assignee: HIKMA PHARMACEUTICALS USA, INC., Berkeley Heights, NJ (US)

( * ) Notice: Subject to any disclaimer, the term of this patent is extended or adjusted under 35 U.S.C. 154(b) by 0 days.

(21) Appl. No.: 17/343,900

(22) Filed: Jun. 10, 2021

(51) Int. Cl.
 *A61K 31/519* (2006.01)
 *A61K 9/48* (2006.01)
 *A61K 9/00* (2006.01)

(52) U.S. Cl.
 CPC .......... *A61K 31/519* (2013.01); *A61K 9/0053* (2013.01); *A61K 9/4858* (2013.01); *A61K 9/4866* (2013.01)

(58) Field of Classification Search
 None
 See application file for complete search history.

(56) References Cited

U.S. PATENT DOCUMENTS

| | | | |
|---|---|---|---|
| 7,514,444 B2 | 4/2009 | Honigberg et al. | |
| 8,008,309 B2 | 8/2011 | Honigberg et al. | |
| 8,476,284 B2 | 7/2013 | Honigberg et al. | |
| 8,497,277 B2 | 7/2013 | Honigberg et al. | |
| 8,563,563 B2 | 10/2013 | Honigberg et al. | |
| 8,697,711 B2 | 4/2014 | Honigberg et al. | |
| 8,703,780 B2 | 4/2014 | Honigberg et al. | |
| 8,735,403 B2 | 5/2014 | Honigberg et al. | |
| 8,754,090 B2 | 6/2014 | Buggy et al. | |
| 8,754,091 B2 | 6/2014 | Honigberg et al. | |
| 8,952,015 B2 | 2/2015 | Honigberg et al. | |
| 8,957,079 B2 | 2/2015 | Honigberg et al. | |
| 8,999,999 B2 | 4/2015 | Buggy et al. | |
| 9,125,889 B2 | 9/2015 | Buggy et al. | |
| 9,181,257 B2 | 11/2015 | Honigberg et al. | |
| 9,296,753 B2 | 3/2016 | Smyth et al. | |
| 9,540,382 B2 | 1/2017 | Purro et al. | |
| 9,713,617 B2 | 7/2017 | Purro et al. | |
| 9,725,455 B1 | 8/2017 | Purro et al. | |
| 9,795,604 B2 | 10/2017 | Byrd et al. | |
| 9,801,881 B2 | 10/2017 | Buggy et al. | |
| 9,801,883 B2 | 10/2017 | Buggy et al. | |
| 9,814,721 B2 | 11/2017 | Buggy et al. | |
| 10,004,746 B2 | 6/2018 | Buggy et al. | |
| 10,016,435 B2 | 7/2018 | Buggy et al. | |
| 10,106,548 B2 | 10/2018 | Purro et al. | |
| 10,125,140 B1 | 11/2018 | Purro et al. | |
| 10,294,231 B2 | 5/2019 | Purro et al. | |
| 10,294,232 B2 | 5/2019 | Purro et al. | |
| 10,463,668 B2 | 11/2019 | Byrd et al. | |
| 10,478,439 B2 | 11/2019 | Honigberg et al. | |
| 10,653,696 B2 | 5/2020 | Buggy et al. | |
| 10,695,350 B2 | 6/2020 | Byrd et al. | |
| 10,751,342 B2 | 8/2020 | Buggy et al. | |
| 10,752,634 B2 | 8/2020 | Purro et al. | |
| 10,961,251 B1 | 3/2021 | Purro et al. | |
| 2016/0287594 A1* | 10/2016 | Gupta | A23L 33/10 |
| 2017/0027941 A1* | 2/2017 | James | A61K 31/436 |
| 2017/0258729 A1 | 9/2017 | Chong et al. | |
| 2020/0171036 A1 | 6/2020 | Gupta et al. | |

FOREIGN PATENT DOCUMENTS

| | | | | |
|---|---|---|---|---|
| CN | 111000806 A | | 4/2020 | |
| KR | 20200127888 A | * | 11/2020 | |
| KR | 20200127888 A | | 11/2020 | |
| WO | WO-2015081180 A1 | * | 6/2015 | ........... A61K 31/519 |
| WO | WO-2017174044 A1 | * | 10/2017 | ........... C07D 487/04 |

OTHER PUBLICATIONS

Khadka et al., "Pharmaceutical particle technologies: An approach to improve drug solubility, dissolution and bioavailability," Asian Journal of Pharmaceutical Sciences, Science Direct, 2014, 13 pages.
International Search Report and Written Opinion issued for International Application No. PCT/US2021/036712 dated Mar. 17, 2022, 14 pages.

* cited by examiner

*Primary Examiner* — Jessica Worsham
(74) *Attorney, Agent, or Firm* — Pearne & Gordon LLP

(57) ABSTRACT

Stable and bioavailable oral dosage forms of ibrutinib, the dosage forms comprising ibrutinib and an acidifying agent. The dosage forms can further comprise a binder, such as sodium alginate, a surfactant, a lubricant, a filler and/or a disintegrant. Methods of treating cancers, particularly blood cancers, and graft versus host disease comprising administering to a patient in need thereof a dosage form comprising ibrutinib and an acidifying agent.

28 Claims, No Drawings

ORAL DOSAGE FORMS OF IBRUTINIB

TECHNICAL FIELD

The invention relates to stable oral dosage forms of ibrutinib as an active ingredient and, in particular, oral dosage forms comprising ibrutinib and acidifying agent.

BACKGROUND

Ibrutinib is a small molecule inhibitor of Bruton's tyrosine kinase (BTK). It forms a covalent bond with a cysteine residue in the BTK active site, leading to the inhibition of BTK enzymatic activity, thus blocking B-cell receptor signaling, which drives B-cells into apoptosis and/or disrupts cell migration and adherence to protective tumor microenvironments. Currently marketed in the US under the trade name IMBRUVICA®, ibrutinib is approved to treat a variety of blood cancers, including mantle cell lymphoma, chronic lymphocytic leukemia, small lymphocytic lymphoma, Waldenström's macroglobulinemia and marginal zone lymphoma, as both a first and second line therapy. Ibrutinib is also indicated as a second line therapy for the treatment of chronic graft versus host disease.

The structure of ibrutinib is illustrated below, having a chemical name of 1-(3R)-3-(4-amino-3-(4-phenoxyphenyl)-1H-pyrazolo[3,4-d]pryimidin-1-yl)prop-2-en-1-one (MW=440.51).

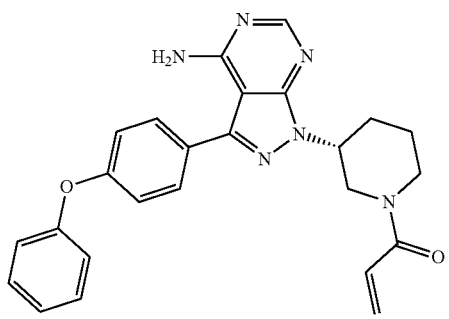 [SMILES: C=CC(=O)N1CCC[C@@H](n2nc(-c3ccc(Oc4ccccc4)cc3)c3c(N)ncnc32)C1]

The active drug substance is practically insoluble in aqueous solutions of pH 4.5-8, and only slightly soluble in HCl at pH 1.2. Based on the solubility characteristics and in vitro permeability experiments, ibrutinib is classified as a BCS Class 2 compound (low solubility and high permeability) which presents a challenge in developing orally bioavailable formulations. The IMBRUVICA® capsule formulation comprises ibrutinib, croscarmellose sodium, microcrystalline cellulose, magnesium stearate and sodium lauryl sulfate encapsulated in a hard gelatin capsule. The IMBRUVICA® tablet formulation comprises ibrutinib, colloidal silicon dioxide, croscarmellose sodium, lactose monohydrate, magnesium stearate, microcrystalline cellulose, povidone and sodium lauryl sulfate with a film coating.

There remains a need for stable oral dosage formulations with enhanced bioavailability given the solubility challenges presented by the active ingredient.

SUMMARY

Described herein are oral dosage forms of ibrutinib that include an acidifying agent such as tartaric acid or citric acid. The dosage forms may further include a binder such as sodium alginate. The inclusion of the acidifying agent is believed to make the microenvironment more acidic, thereby enhancing the dissolution profile of the drug.

In a first aspect of the invention is an oral dosage form comprising ibrutinib and an acidifying agent.

In an example of the first aspect, the acidifying agent is present in an amount of from about 0.5 to about 5.0 weight percent.

In another example of the first aspect, the acidifying agent is present in an amount of from about 1.0 to about 3.0 weight percent.

In yet another example of the first aspect, the acidifying agent is selected from the group consisting of tartaric acid and citric acid.

In still another example of the first aspect, the acidifying agent is tartaric acid.

In another example of the first aspect, the dosage from further comprises a binder.

In another example of the first aspect, the binder is present in an amount of from about 0.5 to about 10.0 weight percent.

In still another example of the first aspect, the binder is present in an amount of from about 1.0 to about 5.0 weight percent.

In yet another example of the first aspect, the binder comprises sodium alginate.

In yet another example of the first aspect, the ibrutinib has a particle size having a $d_{90}$ of from about 75 to about 105 microns.

In still another example of the first aspect, the ibrutinib is Form I ibrutinib.

In yet another example of the first aspect, the oral dosage form is a capsule.

In another example of the first aspect, the oral dosage form releases about 70% or more of the ibrutinib within about 45 minutes when tested in 900 mL of 3.0% w/v Polysorbate 20 in 50 mM phosphate buffer, pH 6.8, paddles at 75 rpm.

In another example of the first aspect, the oral dosage form releases about 90% or more of the ibrutinib within about 45 minutes when tested in 900 mL of 3.0% w/v Polysorbate 20 in 50 mM phosphate buffer, pH 6.8, paddles at 75 rpm.

In another example of the first aspect, the oral dosage form releases about 90% or more of the ibrutinib within about 30 minutes when tested in 900 mL of 3.0% w/v Polysorbate 20 in 50 mM phosphate buffer, pH 6.8, paddles at 75 rpm.

In another example of the first aspect, the oral dosage form releases about 70% or more of the ibrutinib within about 45 minutes when tested in 900 mL of 0.1 N HCl, paddles at 50 rpm.

In another example of the first aspect, the oral dosage form releases about 90% or more of the ibrutinib within about 45 minutes when tested in 900 mL of 0.1 N HCl, paddles at 50 rpm.

In another example of the first aspect, the oral dosage form releases about 90% or more of the ibrutinib within about 30 minutes when tested in 900 mL of 0.1 N HCl, paddles at 50 rpm.

In another example of the first aspect is a method of treating a cancer by administering to a patient in need thereof the oral dosage form of the first aspect.

In still another example of the first aspect, the method of treating cancer is a method of treating a blood cancer by administering to a patient in need thereof the oral dosage form of the first aspect.

In still another example of the first aspect, the method of treating cancer is a method of treating a blood cancer selected from the group consisting of mantle cell lymphoma, chronic lymphocytic leukemia, small lymphocytic lymphoma, Waldenström's macroglobulinemia and marginal zone lymphoma by administering to a patient in need thereof the oral dosage form of the first aspect.

In another example of the first aspect is a method of treating a graft versus host disease by administering to a patient in need thereof the oral dosage form of the first aspect.

In a second aspect is an oral dosage form comprising ibrutinib, an acidifying agent present in an amount of about 1.0 to about 5.0 weight percent and a binder present in an amount of from about 1.0 to about 10 weight percent.

In an example of the second aspect, the acidifying agent is selected from tartaric acid and citric acid and the binder is sodium alginate.

In another example of the second aspect, the oral dosage form further comprises a surfactant, a lubricant, a filler, and a disintegrant.

In another example of the second aspect is a method of treating a cancer by administering to a patient in need thereof the oral dosage form of the second aspect.

In still another example of the second aspect, the method of treating cancer is a method of treating a blood cancer by administering to a patient in need thereof the oral dosage form of the second aspect.

In still another example of the second aspect, the method of treating cancer is a method of treating a blood cancer selected from the group consisting of mantle cell lymphoma, chronic lymphocytic leukemia, small lymphocytic lymphoma, Waldenström's macroglobulinemia and marginal zone lymphoma by administering to a patient in need thereof the oral dosage form of the second aspect.

In another example of the second aspect is a method of treating a graft versus host disease by administering to a patient in need thereof the oral dosage form of the second aspect.

In a third aspect of the disclosure is an oral dosage form consisting essentially of ibrutinib, an acidifying agent, a binder, a surfactant, a lubricant, a filler, and a disintegrant.

In an example of the third aspect, the acidifying agent is present in an amount of from about 1.0 weight percent to about 3.0 weight percent.

In another example of the third aspect, the oral dosage form consists essentially of, or consists of, ibrutinib, tartaric acid or citric acid, sodium alginate, sodium lauryl sulfate, magnesium stearate, a microcrystalline cellulose and croscarmellose sodium.

In still another example of the third aspect, tartaric acid or citric acid is present in an amount of from about 1.0 to about 3.0 weight percent.

In yet another example of the third aspect, sodium alginate is present in an amount of from about 1.0 to about 5.0 weight percent.

In another example of the third aspect, the oral dosage form releases about 70% or more of the ibrutinib within about 45 minutes when tested in 900 mL of 3.0% w/v Polysorbate 20 in 50 mM phosphate buffer, pH 6.8, paddles at 75 rpm.

In still another example of the third aspect, the oral dosage form releases about 90% or more of the ibrutinib within about 45 minutes when tested in 900 mL of 3.0% w/v Polysorbate 20 in 50 mM phosphate buffer, pH 6.8, paddles at 75 rpm.

In still another example of the third aspect, the oral dosage form releases about 90% or more of the ibrutinib within about 30 minutes when tested in 900 mL of 3.0% w/v Polysorbate 20 in 50 mM phosphate buffer, pH 6.8, paddles at 75 rpm In another example of the third aspect, the oral dosage form releases about 70% or more of the ibrutinib within about 45 minutes when tested in 900 mL of 0.1 N HCl, paddles at 50 rpm.

In still another example of the third aspect, the oral dosage form releases about 70% or more of the ibrutinib within about 45 minutes when tested in 900 mL of 0.1 N HCl, paddles at 50 rpm.

In another example of the third aspect, the oral dosage form releases about 90% or more of the ibrutinib within about 30 minutes when tested in 900 mL of 0.1 N HCl, paddles at 50 rpm.

In another example of the third aspect is a method of treating a cancer by administering to a patient in need thereof the oral dosage form of the third aspect.

In still another example of the third aspect, the method of treating cancer is a method of treating a blood cancer by administering to a patient in need thereof the oral dosage form of the third aspect.

In still another example of the third aspect, the method of treating cancer is a method of treating a blood cancer selected from the group consisting of mantle cell lymphoma, chronic lymphocytic leukemia, small lymphocytic lymphoma, Waldenström's macroglobulinemia and marginal zone lymphoma by administering to a patient in need thereof the oral dosage form of the third aspect.

In another example of the third aspect is a method of treating a graft versus host disease by administering to a patient in need thereof the oral dosage form of the third aspect.

DETAILED DESCRIPTION

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the endpoints of each of the ranges are significant both in relation to the other endpoint, and independently of the other endpoint and that ranges include both of the endpoints as well as each of the discreet values therein.

The terms "substantial," "substantially," and variations thereof as used herein are intended to note that a described feature is equal or approximately equal to a value or description. Moreover, "substantially" is intended to denote that two values are equal or approximately equal. In some embodiments, "substantially" may denote values within about 10% of each other, for example within about 5% of each other, or within about 2% of each other.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

As used herein, "weight percent" is a relative measure of the amount of one excipient or ingredient relative to the total weight of the dosage form and is based on the total weight of the dosage form. "Total weight of the dosage form" refers to the total weight of the tablet if the dosage form, including any coating included thereon or to the total weight of the capsule fill. To be clear, the total weight of the dosage form when the dosage form is a capsule does not include the weight of the capsule shell or any coating included thereon.

The present disclosure is directed to oral dosage forms of ibrutinib having good stability and bioavailability compared to commercially available dosage forms. In particular, the dosage forms of the present disclosure comprise ibrutinib and an acidifying agent, such as tartaric acid or citric acid. The dosage forms can further comprise a binder, such as sodium alginate.

The formulations of ibrutinib of the present disclosure are formulated for oral administration. In some examples, the pharmaceutical formulations described herein include, but are not limited to, tablets, capsules, pills, powders, fast melts and multiparticulate formulations; the dosage forms can be formulated for immediate release, controlled release, delayed release, extended release, pulsatile release or mixed immediate and controlled release.

Pharmaceutical compositions may be formulated in a conventional manner using one or more physiologically acceptable carriers including excipients and auxiliaries which facilitate processing of the active compounds into preparations which can be used pharmaceutically. Such processing methods include conventional dry or wet mixing, dissolving, granulating, milling, encapsulating, or compression processes. In one aspect of the disclosure, the oral formulations are made via a standard mixing and blending process.

In one embodiment, pharmaceutical formulations for oral use can be obtained by mixing ibrutinib with one or more solid excipients described herein. The resulting mixture can be compressed into tablets or can be capsulized into hard or soft capsules, such as gelatin capsules. In one example, the oral formulation can by prepared in push-fit capsules, such as a two-piece capsule made of gelatin, hydroxymethylcellulose (HPMC), starch or the like. In addition to ibrutinib, the capsule formulation can comprise one or more pH adjusting agents, binders, carriers, fillers, lubricants, disintegrants, surfactants, wetting agents, stabilizers, antioxidants, preservatives, colorants, flavorings, and/or other pharmaceutically acceptable excipients used in the art. The oral dosage forms described herein may also include a film coating, such as a delayed release coating, which disintegrates upon oral ingestion or upon contact with a biological fluid.

Ibrutinib is a kinase inhibitor first reported in U.S. Pat. No. 7,514,444. Subsequently, a number of polymorphic forms of ibrutinib have been reported, including Forms A, B, C, D, E and F, disclosed in U.S. Pat. No. 9,540,382 and Form I in WO 2015/081180, herein incorporated by reference. The dosage forms of the present disclosure are suitable for use with any polymorphic form of ibrutinib. In one embodiment of the present disclosure, the ibrutinib for use with the disclosed dosage form is Form I of ibrutinib.

Ibrutinib can be included in the dosage form in any amount as would be suitable for therapeutic use. Ibrutinib is currently approved in the US to treat a variety of blood cancers, including mantle cell lymphoma, chronic lymphocytic leukemia, small lymphocytic lymphoma, Waldenström's macroglobulinemia and marginal zone lymphoma, as both a first- and second-line therapy. Ibrutinib is also indicated as a second line therapy for the treatment of chronic graft versus host disease. Ibrutinib can be administered sequentially with or concurrently in combination with one or more other chemotherapeutics. Conventional dosing regimens for ibrutinib are known in the art, but the drug is typically administered orally once per day in a dose amount considered to be therapeutic. By way of example, INMRUVICA® tablets are currently available in dosage amounts of 140 mg, 280 mg, 420 mg, and 560 mg of active pharmaceutical ingredient per tablet. IMBRUVICA® capsules are currently available in dosage amounts of 70 mg and 140 mg of ibrutinib per capsule. The IMBRUVICA® capsules contain Form A ibrutinib and the inactive ingredients of croscarmellose sodium, magnesium stearate, microcrystalline cellulose, and sodium lauryl sulfate in a gelatin shell.

The dosage forms of the present disclosure include a pH adjusting agent. The pH adjusting agent can be any pharmaceutically acceptable acid or base. Suitable pharmaceutically acceptable acids according to the present disclosure include both inorganic acids, for example, hydrochloric, sulfuric, phosphoric, diphosphoric, hydrobromic, hydroiodic and nitric acid, as well as organic acids, for example citric, fumaric, maleic, malic, ascorbic, oxalic, succinic, tartaric, benzoic, acetic, methanesulphonic, ethanesulphonic, benzenesulphonic or p-toluenesulphonic acid, etc. Pharmaceutically acceptable bases can include alkali metal (e.g. sodium or potassium) and alkali earth metal (e.g. calcium or magnesium) hydroxides and organic bases, for example alkyl amines, arylalkyl amines and heterocyclic amines. The dosage forms of the present disclosure can include one or more pH adjusting agents, for example, a combination of one, two, three or more suitable acids. In a preferred example according to the disclosure, the dosage form includes a pharmaceutically acceptable acid, in particular, tartaric acid or citric acid.

The pH adjusting agent can be present in any amount as necessary to affect the pH of the surrounding microenvironment. In particular, the pH adjusting agent (acid or base) can be present in an amount of about 0.5 to about 10.0 weight percent, for example about 0.5 weight percent, about 1.0 weight percent, about 1.5 weight percent, about 2.5 weight percent, about 3.0 weight percent, about 3.5 weight percent, about 4.0 weight percent, about 4.5 weight percent, about 5.0 weight percent, about 5.5 weight percent, about 6.0 weight percent, about 6.5 weight percent, about 7.0 weight percent, about 7.5 weight percent, about 8.0 weight percent, about 8.5 weight percent, about 9.0 weight percent, about 9.5 weight percent, or about 10.0 weight percent, of the total weight of the dosage form. In one example, the pH adjusting is a pharmaceutically acceptable acid present in an amount of from about 0.5 to about 5.0 weight percent of the total weight of the dosage form. In another example, the pH adjusting agent is a pharmaceutically acceptable acid present in an amount of from about 0.5 to about 3.0 weight percent of the total weight of the dosage form. In another example, the pH adjusting agent is a pharmaceutically acceptable acid present in an amount of from about 1.0 to about 2.0 weight percent of the total weight of the dosage form. In another example, the pH adjusting agent is citric acid or tartaric acid present in an amount of about 0.5 weight percent, about 1.0 weight percent, about 1.5 weight percent, about 2.5 weight percent, or about 3.0 weight percent of the total weight of the dosage form. In one embodiment, the pH adjusting agent is tartaric acid present in an amount of about 0.5 to about 3.0 weight percent. In another embodiment, the pH adjusting agent is tartaric acid present in an amount of about 0.5 weight percent of the total weight of the dosage form. In another embodiment, the pH adjusting agent is tartaric acid present in an amount of about 1.0 weight percent. In yet another embodiment, the pH adjusting agent is tartaric acid present in an amount of about 1.5 weight percent. In still another embodiment, the pH adjusting agent is tartaric acid present in an amount of about 2.0 weight percent of the total weight of the dosage form. In another embodiment, the pH adjusting agent is tartaric acid present in an amount of about 2.5 weight percent. In still another embodiment, the pH adjusting agent is tartaric acid present in an amount of about 3.0 weight percent.

Suitable binders according to the present invention include, e.g., amylose, bentonites, cellulose and cellulose derivatives such as carboxymethylcellulose, methylcellulose, HPMC, HPMCAS, hydroxyethylcellulose, hydroxypropylcellulose, ethylcellulose, and microcrystalline cellulose (MCC), crospovidone, dextrin, gelatin, natural or synthetic gums, magnesium aluminum silicate, microcrystalline dextrose, pregelatinized starch, polyethylene glycol, polysaccharide acids, polyvinylpyrrolidone, polyvinylpyrrolidone/vinyl acetate copolymer, povidone, sodium alginate, starches, sugars (e.g. sucrose, glucose, dextrose, molasses, mannitol, sorbitol, xylitol, lactose), tragacanth, waxes, and the like. In one example according to the disclosure, the dosage form includes sodium alginate.

Binders can be included in the dosage form in any amount useful for holding together the ingredients of the dosage form. The amount of binder included in an oral dosage form, and in particular for a capsule dosage form, is typically more than about 20 weight percent based on the total weight of the dosage form, e.g. 20 to 70 weight percent. It was surprisingly found that the inclusion of a pH adjusting agent in the form of an acid in combination with a lower amount of binder than would be otherwise be expected provided an oral dosage form having an in vitro dissolution profile that is highly similar to that of the brand product. The dosage forms according to the present disclosure can include much lower amounts of binder, for example, about 1.0 to about 10.0 weight percent, for example, about 1.0 weight percent, about 1.5 weight percent, about 2.5 weight percent, about 3.0 weight percent, about 3.5 weight percent, about 4.0 weight percent, about 4.5 weight percent, about 5.0 weight percent, about 5.5 weight percent, about 6.0 weight percent, about 6.5 weight percent, about 7.0 weight percent, about 7.5 weight percent, about 8.0 weight percent, about 8.5 weight percent, about 9.0 weight percent, about 9.5 weight percent, or about 10.0 weight percent, of the total weight of the dosage form. In one embodiment, the dosage forms according to the present disclosure include a binder in an amount of about 1.0 to about 5.0 weight percent. In another example, the binder is sodium alginate present in an amount of about 1.0 weight percent, about 1.5 weight percent, about 2.5 weight percent, about 3.0 weight percent, about 3.5 weight percent, about 4.0 weight percent, about 4.5 weight percent, or about 5.0 weight percent of the total weight of the dosage form. In one embodiment, the binder is sodium alginate present in an amount of about 3.0 weight percent.

Suitable carriers for use in the oral dosage forms described herein include, but are not limited to, gelatin, colloidal silicon dioxide, silicified colloidal silicon dioxide, calcium glycerophosphate, calcium lactate, maltodextrin, glycerin, magnesium silicate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose (HPMC), hydroxypropylmethylcellulose acetate stearate (HPMCAS), sucrose, microcrystalline cellulose (MCC), lactose, mannitol and the like. The pharmaceutical dosage forms of the present disclosure can comprise from about 1 to about 70 weight percent of a carrier.

Suitable filling agents, or fillers, for use in the solid dosage forms described herein include, but are not limited to, calcium carbonate, calcium phosphate, dibasic calcium phosphate, calcium sulfate, lactose, microcrystalline cellulose (MCC), silicified MCC (e.g. ProSolv® HD90), cellulose powder, dextrose, dextran, starches, pregelatinized starch, hydroxypropylmethylcellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like. In one example of the disclosed formulation, the filler is silicified MCC. The pharmaceutical compositions provided herein may contain from about 1 to about 70 weight percent of a filler.

Suitable disintegrants for use in the solid dosage forms described herein include, but are not limited to, an alginate such as alginic acid or a salt of alginic acid such as sodium alginate, bentonite, a cellulose such as microcrystalline cellulose, methylcellulose, croscarmellose, or a cross-linked cellulose, such as cross-linked sodium carboxymethylcellulose, cross-linked carboxymethylcellulose, or cross-linked croscarmellose, a cross-linked starch such as sodium starch glycolate, a gum, e.g. agar, guar, or locust bean, magnesium aluminum silicate, natural starches such as corn starch or potato starch, a pregelatinized starch, or sodium starch glycolate, a cross-linked polymer such as crospovidone, a cross-linked polyvinylpyrrolidone, and/or sodium starch glycolate. In one example provided herein, the disintegrating agent is croscarmellose sodium. The amount of disintegrant varies depending on the type of formulation. The pharmaceutical compositions provided herein may contain, in one example, from about 0.5 to about 15 weight percent or from about 10 to about 15 weight percent of a disintegrant.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, boric acid, sodium benzoate, sodium acetate, sodium chloride, leucine, a polyethylene glycol or a methoxypolyethylene glycol, PEG 4000, PEG 5000, PEG 6000, propylene glycol, sodium oleate, glyceryl behenate, glyceryl palmitostearate, glyceryl benzoate, magnesium or sodium lauryl sulfate, and the like. In some embodiments provided herein, the lubricant is magnesium stearate. The pharmaceutical compositions provided herein may contain about 0.1 to about 5 weight percent of a lubricant.

Suitable diluents for use in the solid dosage forms described herein include, but are not limited to, cellulose and cellulose derivatives (such as microcrystalline cellulose, silicified MCC, microcellulose, etc.), cyclodextrins, polyols (including mannitol, xylitol, and sorbitol), polysaccharides (for example dextrates and maltodextrin), starches, modified starches, sugars (e.g. lactose, sucrose, and dextrose), talc, and the like. The amount of diluent varies depending on the type of formulation. The pharmaceutical compositions provided herein may contain from about 1.0 to about 70 weight percent of a diluent.

Suitable surfactants or wetting agents, include copolymers of ethylene oxide and propylene oxide, e.g., Pluronic®

(BASF), glyceryl monostearate, magnesium stearate, oleic acid, polaxomers, polyoxyethylene sorbitan monooleate, polyoxyethylene sorbitan monolaurate, polysorbates, quaternary ammonium compounds (e.g., Polyquat 10®), sodium lauryl sulfate, sodium oleate, sorbitan monolaurate, sorbitan monooleate, triacetin, triethanolamine oleate, vitamin E TPGS and the like. In some embodiments according to the disclosure, the surfactant is sodium lauryl sulfate. The pharmaceutical compositions provided herein may contain about 0.1 to about 5 weight percent of a surfactant or wetting agent.

According to the disclosure, the ibrutinib dosage forms can include a stabilizer, including but not limited to an antioxidant or a preservative. Suitable stabilizers for use in the solid dosage forms described herein include but are not limited to butylated hydroxytoluene (BHT), sodium ascorbate, and tocopherol. The pharmaceutical compositions provided herein may contain about 0.1 to about 5 weight percent of a stabilizer.

EXAMPLES

Particle Size Selection

As ibrutinib has limited solubility in different buffers, the particle size of the API was selected to obtain the desired dissolution and to ensure smooth processing of the final dosage form to obtain a finished dosage form that meets specifications.

All capsules were manufacturing via a dry granulation method by slugging followed by capsule filling. Prosolv HD90 and SLS were first sifted using a 500-micron sieve, and then mixed with ibrutinib in a plastic bag. The resulting mixture was passed through a 500-micron sieve. Sodium alginate was sifted into the sifted API mixture, followed by Ac-di-sol® (croscarmellose sodium), acidifying agent (tartaric acid or citric acid). The resulting mixture was sieved and loaded into a Matcon container and mixed. To this mixture was added part of the magnesium stearate and sieved through a 500-micron filter. The prepared powder mix was then prepared into slugs. The resulting slugs were passed through mesh R.25 using a Glatt crushing machine and collected. The resulting mixture was passed through mesh S1.0 using a Glatt crushing machine before being transferred to the Matcon container and mixed. The remaining magnesium stearate was mixed with a small quantity of the premix and the entire mixture combined and mixed to obtain a powder blend. The powder blend was filled into empty gelatin capsules (size 0) using a filling machine.

Particle size was evaluated by testing dissolution profiles of micronized ($d_{90}$=25 microns) and non-micronized ($d_{90}$=75 microns) Form I ibrutinib in a test formulation as detailed in Table 1 below. All of the prepared formulations were evaluated in the recommended FDA drug release medium (3.0% w/v Polysorbate 20 in 50 mM phosphate buffer, pH 6.8, paddles, 75 rpm, 900 mL) as well as in 0.1 N HCl (paddles, 50 rpm, 900 mL) and compared to a brand IMBRUVICA® 140 mg capsule for similarity. A similarity factor (F2) was calculated for each test capsule relative to a Comparative Example, the Comparative Example capsule being the 140 mg RLD product which is branded as IMBRUVICA® and contains ibrutinib, croscarmellose sodium, microcrystalline cellulose, magnesium stearate and sodium lauryl sulfate encapsulated in a hard gelatin capsule. An F2 value closer to 100 indicates performance closer to the brand product, and above 50 is considered "passing".

TABLE 1

Formulation composition for API particle size determination

| Ingredient | Non-Micronized API ($d_{90}$ = 75 microns) mg/capsule (%) | Micronized API ($d_{90}$ = 25 microns) mg/capsule (%) |
| --- | --- | --- |
| Ibrutinib Form I | 140.0 (42.4) | 140.0 (42.4) |
| Prosolv ® HD 90 (silicified MCC) | 152.05 (46.1) | 152.05 (46.1) |
| Croscarmellose Sodium (intra) | 16.5 (5.0) | 16.5 (5.0) |
| Sodium Lauryl Sulfate | 9.9 (3.0) | 9.9 (3.0) |
| Croscarmellose Sodium (extra) | 9.9 (3.0) | 9.9 (3.0) |
| Magnesium Stearate | 1.65 (0.5) | 1.65 (0.5) |
| Total weight (mg) | 330.0 = (100%) | 330.0 = (100%) |

TABLE 2

Percent drug release for particle size determination in 3% w/v Polysorbate in phosphate buffer

| Time (min) | Non-Micronized API ($d_{90}$ = 75 microns) | Micronized API ($d_{90}$ = 25 microns) | Comparative Example |
| --- | --- | --- | --- |
| 5 | 32.6 | 22.1 | 40.1 |
| 10 | 63.4 | 58.7 | 69.1 |
| 15 | 75.5 | 77.0 | 81.1 |
| 30 | 91.3 | 94.5 | 95.9 |
| 45 | 97.6 | 100.3 | 100.2 |
| Similarity Factor (F2) | 63 | 51 | — |

TABLE 3

Percent drug release for particle size determination in 0.1 N HCl

| Time (min) | Non-Micronized API ($d_{90}$ = 75 micron) | Micronized API ($d_{90}$ = 25 micron) | Comparative Example |
| --- | --- | --- | --- |
| 5 | 42.5 | 27.2 | 42.3 |
| 10 | 61.5 | 57.0 | 62.6 |
| 15 | 64.8 | 63.5 | 65.9 |
| 30 | 69.2 | 76.5 | 70.7 |
| 45 | 70.5 | 79.5 | 72.4 |
| Similarity Factor (F2) | 89 | 54 | — |

As seen in Tables 2 and 3, the formulations with ibrutinib having a particle size of $d_{90}$ around 75 microns had dissolution profiles that more closely resembled that of the brand product than did the micronized API with the smaller particle size. The difference between the non-micronized API and the micronized API was more pronounced in the 0.1 N HCl dissolution medium (F2 of 89 vs. 54, respectively) as compared to the FDA recommended dissolution medium (F2 of 63 vs. 51, respectively). The final API particle size specifications for use with the dosage forms tested herein were $d_{90}$ 75-105 microns.

Excipient Selection

Addition of an Acid

Since ibrutinib is a basic drug and its solubility higher in an acidic environment (data not shown), addition of an acid to the formulation was contemplated to determine whether it would enhance the dissolution in in vitro testing. Tartaric acid was added to the composition. Without wishing to be bound by theory, it is believed that inclusion of an acid in the oral formulation results in a more acidic microenvironment, thereby improving dissolution and drug release. Capsules comprising 2.0 wt tartaric acid were prepared and tested for release compared to otherwise identical capsules without the acid as described above. The capsule formulations are detailed in Table 4 below, and the dissolution profiles in Tables 5 and 6.

TABLE 4

Formulation composition for acid effect

| Ingredient | mg/capsule (wt %) | |
|---|---|---|
| Ibrutinib Form I | 140.0 (28) | 140.0 (27.5) |
| Prosolv ® HD 90 (silicified MCC) | 283.0 (56.6) | 283.0 (55.5) |
| Tartaric Acid | 0 | 10.0 (2.0) |
| Croscarmellose Sodium | 60.0 (12.0) | 60.0 (11.8) |
| Sodium Lauryl Sulfate | 7.0 (1.4) | 7.0 (1.4) |
| Magnesium Stearate | 10 (2.0) | 10 (2.0) |
| Total weight (mg) | 500.0 | 510.0 |

TABLE 5

Percent drug release for acid effect in 3% w/v Polysorbate in phosphate buffer

| Time (min) | 0 wt % tartaric acid | 2.0 wt % tartaric acid | Comparative Example |
|---|---|---|---|
| 10 | 75.1 | 65.7 | 66.3 |
| 15 | 85.9 | 74.9 | 77.4 |
| 30 | 95.8 | 88.1 | 92.8 |
| 45 | 100.2 | 93.4 | 99.5 |
| Similarity Factor (F2) | 60 | 69 | — |

TABLE 6

Percent drug release for acid effect in 0.1 N HCl

| Time (min) | 0 wt % tartaric acid | 2.0 wt % tartaric acid | Comparative Example |
|---|---|---|---|
| 10 | 78.0 | 74.3 | 59.3 |
| 15 | 84.1 | 75.5 | 66.2 |
| 30 | 91.8 | 79.9 | 72.6 |
| 45 | 94.8 | 91.9 | 74.7 |
| Similarity Factor (F2) | 36 | 50 | — |

From the data in Tables 5 and 6, it can be seen that in both mediums, the capsules including tartaric acid provided for higher F2 values, indicating a more similar release profile to the Comparative Example as compared to the formulation without tartaric acid.

To test the effect of acid selection, tartaric acid and citric acid were tested to examine the identity of the acidifying agent on the dissolution profile of ibrutinib capsules. Test capsules according to Table 7 below were made and dissolution profiles measured (Tables 8 and 9) as described above.

TABLE 7

Formulation composition for acid effect

| Ingredient | Tartaric Acid | Citric Acid |
|---|---|---|
| | mg/capsule (wt %) | |
| Ibrutinib Form I | 140.0 (26.4) | 140.0 (26.4) |
| Prosolv ® HD 90 (silicified MCC) | 278.5 (52.4) | 278.5 (52.4) |

TABLE 7-continued

Formulation composition for acid effect

| Ingredient | Tartaric Acid | Citric Acid |
|---|---|---|
| | mg/capsule (wt %) | |
| Sodium Alginate | 10.4 (2.0) | 10.4 (2.0) |
| Acid | 21.0 (4.0) | 21.0 (4.0) |
| Croscarmellose Sodium | 62.4 (11.8) | 62.4 (11.8) |
| Sodium Lauryl Sulfate | 7.3 (1.4) | 7.3 (1.4) |
| Magnesium Stearate (extra) | 10.4 (2.0) | 10.4 (2.0) |
| Total weight (mg) | 530.0 | 530.0 |

TABLE 8

Percent drug release for acid effect in 3% w/v Polysorbate in phosphate buffer

| Time (min) | Tartaric Acid | Citric Acid | Comparative Example |
|---|---|---|---|
| 10 | 63.8 | 69.3 | 66.3 |
| 15 | 83.6 | 86.9 | 77.4 |
| 30 | 96.3 | 101.7 | 92.8 |
| 45 | 99.2 | 103.8 | 99.5 |
| Similarity Factor (F2) | 70 | 57 | — |

TABLE 9

Percent drug release for acid effect in 0.1 N HCl

| Time (min) | Tartaric Acid | Citric Acid | Comparative Example |
|---|---|---|---|
| 10 | 57.3 | 54.9 | 59.3 |
| 15 | 65.8 | 64.0 | 66.2 |
| 30 | 76.8 | 75.5 | 72.6 |
| 45 | 81.6 | 80.3 | 74.7 |
| Similarity Factor (F2) | 68 | 69.24 | — |

Both of the capsules comprising tartaric acid and citric acid resulted in passing F2 values in both dissolution testing mediums, with the tartaric acid-containing capsule performing slightly better in the Polysorbate medium. Thus, tartartic acid was chosen for further development.

To determine the optimal amount of acid for inclusion into the capsules, the API release profiles of capsules comprising varying amounts of tartaric acid (0 wt. % 1 wt. % 2 wt. %, and 3 wt. %) were tested. Test capsules according to Table 10 below were made and dissolution profiles measured (Tables 11 and 12) as described above.

TABLE 10

Formulation composition for acid quantity

| Ingredient | 0 wt % tartaric acid | 1 wt % tartaric acid | 2 wt % tartaric acid | 3 wt % tartaric acid |
|---|---|---|---|---|
| | mg/capsule (wt %) | | | |
| Ibrutinib Form I | 140.0 (26.4) | 140.0 (26.4) | 140.0 (26.4) | 140.0 (26.4) |
| Prosolv ® HD 90 (silicified MCC) | 283.6 (53.5) | 288.7 (54.4) | 283.6 (53.5) | 278.1 (52.4) |
| Sodium Alginate | 15.9 (3.0) | 15.9 (3.0) | 15.9 (3.0) | 15.9 (3.0) |
| Tartaric Acid | 0 | 5.3 (1.0) | 10.4 (2.0) | 15.9 (3.0) |
| Croscarmellose Sodium | 72.8 (13.7) | 62.4 (11.8) | 62.4 (11.8) | 62.4 (11.8) |
| Sodium Lauryl Sulfate | 7.3 (1.4) | 7.3 (1.4) | 7.3 (1.4) | 7.3 (1.4) |
| Magnesium Stearate | 10.4 (2.0) | 10.4 (2.0) | 10.4 (2.0) | 10.4 (2.0) |
| Total weight (mg) | 530.0 | 530.0 | 530.0 | 530.0 |

TABLE 11

Percent drug release for variation in amount of acid in 3% w/v Polysorbate in phosphate buffer

| Time (min) | 1 wt % tartaric acid | 2 wt % tartaric acid | 3 wt % tartaric acid | Comparative Example |
|---|---|---|---|---|
| 10 | 56.3 | 58.4 | 54.3 | 66.3 |
| 15 | 75.8 | 76.6 | 77.2 | 77.4 |
| 30 | 91.9 | 96.0 | 93.8 | 92.8 |
| 45 | 97.3 | 100.5 | 97.7 | 99.5 |
| Similarity Factor (F2) | 64 | 68 | 61 | — |

TABLE 12

Percent drug release for variation in amount of acid in 0.1 N HCl

| Time (min) | 0 wt % tartaric acid | 2 wt % tartaric acid | Comparative Example |
|---|---|---|---|
| 10 | 40.4 | 51.0 | 59.3 |
| 15 | 53.3 | 59.8 | 66.2 |
| 30 | 67.4 | 72.9 | 72.6 |
| 45 | 73.4 | 78.8 | 74.7 |
| Similarity Factor (F2) | 46 | 62 | — |

All three formulations comprising tartaric acid resulted in passing F2 values in the FDA recommended medium, with the highest F2 value observed for 2% tartaric acid (68).

Notably, consistent with the data above, Table 12 demonstrates that the formulation comprising 2 wt % tartaric acid performed significantly better than did the formulation that did not contain any tartaric acid, despite that formulation having a higher amount of disintegrant.

Disintegrant

Croscarmellose sodium (CCS) was selected as the disintegrant for the development of the ibrutinib capsules according to the present disclosure, and the dissolution profile was monitored for capsules comprising 10%, 11.8% and 14% by weight. The capsules detailed in Table 13 below were prepared as described above and tested in the 3.0) w/v Polysorbate 20 in 50 mM phosphate buffer and in 0.1 N HCL. The results of the dissolution tests are shown in Tables 14 and 15.

TABLE 13

Formulation composition for disintegrant variation

| Ingredient | 10 wt % CCS | 11.8 wt % CCS | 14 wt % CCS |
|---|---|---|---|
| | mg/capsule (wt %) | | |
| Ibrutinib Form I | 140.0 (26.4) | 140.0 (26.4) | 140.0 (26.4) |
| Prosolv ® HD 90 (silicified MCC) | 293.0 (55.3) | 271.8 (51.3) | 283.6 (53.5) |
| Sodium Alginate | 15.9 (3.0) | 15.9 (3.0) | 15.9 (3.0) |
| Tartaric Acid | 10.4 (2.0) | 10.4 (2.0) | 10.4 (2.0) |
| Croscarmellose Sodium | 53.0 (10.0) | 74.2 (14.0) | 62.4 (11.8) |
| Sodium Lauryl Sulfate | 7.3 (1.4) | 7.3 (1.4) | 7.3 (1.4) |
| Magnesium Stearate | 10.4 (2.0) | 10.4 (2.0) | 10.4 (2.0) |
| Total weight (mg) | 530.0 | 530.0 | 530.0 |

TABLE 14

Percent drug release for disintegrant variation in 3% w/v Polysorbate in phosphate buffer

| Time (min) | 10 wt % CCS | 11.8 wt % CCS | 14 wt % CCS | Comparative Example |
|---|---|---|---|---|
| 10 | 57.0 | 58.4 | 50.6 | 66.3 |
| 15 | 75.5 | 76.6 | 76.6 | 77.4 |
| 30 | 90.8 | 96.0 | 93.8 | 92.8 |
| 45 | 95.6 | 100.5 | 97.5 | 99.5 |
| Similarity Factor (F2) | 64 | 68 | 55 | — |

TABLE 15

Percent drug release for disintegrant variation in 0.1 N HCl

| Time (min) | 10 wt % CCS | 11.8 wt % CCS | 14 wt % CCS | Comparative Example |
|---|---|---|---|---|
| 10 | 46.5 | 51.0 | 42.6 | 59.3 |
| 15 | 54.3 | 59.8 | 54.5 | 66.2 |
| 30 | 66.5 | 72.9 | 73.3 | 72.6 |
| 45 | 72.6 | 78.7 | 81.6 | 74.7 |
| Similarity Factor (F2) | 51 | 62 | 48 | — |

As seen in Table 14, all three formulations resulted in a passing F2 value for dissolution in the 3% w/v Polysorbate in phosphate buffer. API release in the 0.1 N HCl solution (Table 15) was most similar to the RLD brand capsules for the test capsules comprising 11.8 wt % CCS, which was also the highest F2 value for dissolution in the FDA recommended Polysorbate solution (F2=68).

Binder

In order to improve on the release profiles and make them more similar to the brand, addition of a binder to the acid-containing formulation was contemplated in order to slow the release. Sodium alginate was selected as the binder for the development of the ibrutinib capsules for its desirable hard and compact slugs, resulting in granules with good flow properties. Three batches testing varying amounts of sodium alginate were made according to the present disclosure, and the dissolution profile was monitored for capsules comprising 2%, 3%, and 4% by weight. The capsules detailed in Table 16 below were prepared as described above and tested in the 3.0% w/v Polysorbate 20 in 50 mM phosphate buffer and in 0.1 N HCL. The results of the dissolution tests are shown in Tables 17 and 18.

TABLE 16

Formulation composition for binder variation

| Ingredient | 2 wt % sodium alginate | 3 wt % sodium alginate | 4 wt % sodium alginate |
|---|---|---|---|
| | mg/capsule (wt %) | | |
| Ibrutinib Form I | 140.0 (26.4) | 140.0 (26.4) | 140.0 (26.4) |
| Prosolv ® HD 90 (silicified MCC) | 288.9 (54.5) | 283.6 (53.5) | 278.3 (52.5) |
| Sodium Alginate | 10.6 (2.0) | 15.9 (3.0) | 21.2 (4.0) |
| Tartaric Acid | 10.4 (2.0) | 10.4 (2.0) | 10.4 (2.0) |
| Croscarmellose Sodium | 62.4 (11.8) | 62.4 (11.8) | 62.4 (11.8) |
| Sodium Lauryl Sulfate | 7.3 (1.4) | 7.3 (1.4) | 7.3 (1.4) |
| Magnesium Stearate (extra) | 10.4 (2.0) | 10.4 (2.0) | 10.4 (2.0) |
| Total weight (mg) | 530.0 | 530.0 | 530.0 |

TABLE 17

Percent drug release for binder amount variation in 3% w/v Polysorbate in phosphate buffer

| Time (min) | 2 wt % sodium alginate | 3 wt % sodium alginate | 4 wt % sodium alginate | Comparative Example |
|---|---|---|---|---|
| 10 | 71.8 | 58.4 | 52.5 | 66.3 |
| 15 | 81.4 | 76.6 | 74.7 | 77.4 |
| 30 | 91.1 | 96.0 | 92.3 | 92.8 |
| 45 | 95.0 | 100.5 | 97.5 | 99.5 |
| Similarity Factor (F2) | 68 | 68 | 57 | — |

TABLE 18

Percent drug release for binder amount variation in 0.1 N HCl

| Time (min) | 2 wt % sodium alginate | 3 wt % sodium alginate | 4 wt % sodium alginate | Comparative Example |
|---|---|---|---|---|
| 10 | 52.8 | 51.0 | 30.0 | 59.3 |
| 15 | 64.0 | 59.8 | 37.4 | 66.2 |
| 30 | 75.6 | 72.9 | 48.6 | 72.6 |
| 45 | 81.7 | 78.7 | 54.5 | 74.7 |
| Similarity Factor (F2) | 64 | 62 | 29 | — |

As seen in Tables 17 and 18, the formulations with 2 wt % and 3 wt % sodium alginate show desirable release patterns and gave passing F2 values in both dissolution mediums. The capsule preparation comprising 3 wt 0 sodium alginate demonstrated better physical properties compared to the 2 wt % capsules.

Wetting Agent

Sodium lauryl sulfate (SLS) was selected as the wetting agent for the development of the ibrutinib capsules. SLS levels were tested at 1.2 wt %, 1.4 wt %, and 1.6 wt % SLS (Table 19). The release profile of each capsule was monitored as described above (Tables 20 and 21).

TABLE 19

Formulation composition for SLS amount variation

| Ingredient | 1.2 wt % SLS | 1.4 wt % SLS | 1.6 wt % SLS |
|---|---|---|---|
| | mg/capsule (wt %) | | |
| Ibrutinib Form I | 140.0 (26.4) | 140.0 (26.4) | 140.0 (26.4) |
| Prosolv ® HD 90 (silicified MCC) | 284.7 (53.7) | 283.6 (53.5) | 282.6 (53.3) |
| Sodium Alginate | 15.9 (3.0) | 15.9 (3.0) | 15.9 (3.0) |
| Tartaric Acid | 10.4 (2.0) | 10.4 (2.0) | 10.4 (2.0) |
| Croscarmellose Sodium | 62.4 (11.8) | 62.4 (11.8) | 62.4 (11.8) |
| Sodium Lauryl Sulfate | 6.2 (1.2) | 7.3 (1.4) | 8.32 (1.6) |
| Magnesium Stearate | 10.4 (2.0) | 10.4 (2.0) | 10.4 (2.0) |
| Total weight (mg) | 530.0 | 530.0 | 530.0 |

TABLE 20

Percent drug release for SLS amount variation in 3% w/v Polysorbate in phosphate buffer

| Time (min) | 1.2 wt % SLS | 1.4 wt % SLS | 1.6 wt % SLS | Comparative Example |
|---|---|---|---|---|
| 10 | 61.0 | 58.4 | 58.0 | 66.3 |
| 15 | 82.2 | 76.6 | 73.0 | 77.4 |
| 30 | 94.9 | 96.0 | 88.2 | 92.8 |

TABLE 20-continued

Percent drug release for SLS amount variation in 3% w/v Polysorbate in phosphate buffer

| Time (min) | 1.2 wt % SLS | 1.4 wt % SLS | 1.6 wt % SLS | Comparative Example |
|---|---|---|---|---|
| 45 | 98.0 | 100.5 | 95.3 | 99.5 |
| Similarity Factor (F2) | 70 | 68 | 62 | — |

TABLE 21

Percent drug release for SLS amount variation in 0.1 N HCl

| Time (min) | 1.2 wt % SLS | 1.4 wt % SLS | 1.6 wt % SLS | Comparative Example |
|---|---|---|---|---|
| 10 | 37.8 | 51.0 | 45.2 | 59.3 |
| 15 | 47.5 | 59.8 | 56.1 | 66.2 |
| 30 | 61.9 | 72.9 | 68.8 | 72.6 |
| 45 | 67.1 | 78.7 | 74.5 | 74.7 |
| Similarity Factor (F2) | 40 | 62 | 52 | — |

As seen in Tables 20 and 21, all three SLS variations gave passing F2 values in the Polysorbate medium. The capsules comprising 1.4 wt. 0 SLS provided the highest F2 value (F2=62) in 0.1 N HCl.

Lubricant

Magnesium stearate was selected as the lubricant for the development of the ibrutinib capsules. Magnesium stearate levels were tested at 1.5 wt %, 2.0 wt %, and 2.5 wt % (Table 22). The release profile of each capsule was monitored as described above (Tables 23 and 24).

TABLE 22

Formulation composition for magnesium stearate amount variation

| Ingredient | 1.5 wt % Mg stearate | 2.0 wt % Mg stearate mg/capsule (wt %) | 2.5 wt % Mg stearate |
|---|---|---|---|
| Ibrutinib Form I | 140.0 (26.4) | 140.0 (26.4) | 140.0 (26.4) |
| Prosolv ® HD 90 (silicified MCC) | 286.0 (54.0) | 283.6 (53.5) | 280.7 (53.0) |
| Sodium Alginate | 15.9 (3.0) | 15.9 (3.0) | 15.9 (3.0) |
| Tartaric Acid | 10.4 (2.0) | 10.4 (2.0) | 10.4 (2.0) |
| Croscarmellose Sodium | 62.4 (11.8) | 62.4 (11.8) | 62.4 (11.8) |
| Sodium Lauryl Sulfate | 7.3 (1.4) | 7.3 (1.4) | 7.3 (1.4) |
| Magnesium Stearate | 8.0 (1.5) | 10.4 (2.0) | 13.25 (2.5) |
| Total weight (mg) | 530.0 | 530.0 | 530.0 |

TABLE 23

Percent drug release for magnesium stearate amount variation in 3% w/v Polysorbate in phosphate buffer

| Time (min) | 1.5 wt % Mg stearate | 2.0 wt % Mg stearate | 2.5 wt % Mg stearate | Comparative Example |
|---|---|---|---|---|
| 10 | 61.9 | 58.4 | 50.7 | 66.3 |
| 15 | 81.8 | 76.6 | 78.0 | 77.4 |
| 30 | 93.9 | 96.0 | 94.5 | 92.8 |
| 45 | 99.6 | 100.5 | 100.4 | 99.5 |
| Similarity Factor (F2) | 74 | 68 | 55 | — |

TABLE 24

Percent drug release for magnesium stearate amount variation in 0.1 N HCl

| Time (min) | 1.5 wt % Mg stearate | 2.0 wt % Mg stearate | 2.5 wt % Mg stearate | Comparative Example |
|---|---|---|---|---|
| 10 | 36.6 | 51.0 | 40.4 | 59.3 |
| 15 | 47.8 | 59.8 | 46.7 | 66.2 |
| 30 | 57.9 | 72.9 | 61.1 | 72.6 |
| 45 | 63.6 | 78.7 | 66.7 | 74.7 |
| Similarity Factor (F2) | 38 | 62 | 41 | — |

As seen in Tables 23 and 24, while all three magnesium stearate variations gave passing F2 values in the Polysorbate medium, the 2.0 wt % composition gave the most similar release to the brand product (F2=62) in the 0.1 N HCl dissolution medium.

Stability Studies

The capsules comprising ibrutinib and tartaric acid according to the present disclosure were tested for stability Capsules according to the formulation provided in Table 25 (below) were prepared as described above.

TABLE 25

Capsule formulation for stability testing

| Ingredient | function | mg/capsule | % wt |
|---|---|---|---|
| Ibrutinib Form I | API | 140.0 | 26.4 |
| Prosolv ® HD 90 (silicified MCC) | filler | 283.6 | 53.5 |
| Sodium Alginate | binder | 15.9 | 3.0 |
| Tartaric Acid | pH adjuster | 10.4 | 2.0 |
| Croscarmellose Sodium | disintegrant | 62.4 | 11.8 |
| Sodium Lauryl Sulfate | wetting agent | 7.3 | 1.4 |
| Magnesium Stearate | lubricant | 10.4 | 2.0 |
| Total weight (mg) | | 530.0 | |

The stability of the encapsulated API following 3 mo storage at 30° C./65% RH and 40° C./75% RH was tested. Under both sets of storage conditions, the API was determined to be greater than 97% pure by HPLC and dissolution studies determined the API to be more than 95% released within 30 minutes (data not shown), well within specifications for the ibrutinib product.

Many variations and modifications may be made to the above-described embodiments of the disclosure without departing substantially from the spirit and various principles of the disclosure. All such modifications and variations are intended to be included herein within the scope of this disclosure and protected by the following claims.

What is claimed is:

1. A solid oral dosage formulation comprising ibrutinib and an acidifying agent, wherein the ibrutinib has a particle size $d_{90}$ of from about 75 to about 105 microns, and wherein the oral dosage formulation releases about 70% or more of the ibrutinib within about 45 minutes when measured in either 900 mL of 3.0% w/v Polysorbate 20 in 50 mM phosphate buffer, pH 6.8, paddles at 75 rpm or 900 mL of 0.1 N HCl, paddles at 50 rpm.

2. The oral dosage formulation of claim 1, wherein the acidifying agent is present in an amount of from about 0.5 to about 5.0 weight percent.

3. The oral dosage formulation of claim 2, wherein the acidifying agent is present in an amount of from about 1.0 to about 3.0 weight percent.

4. The oral dosage formulation of claim 1, wherein the acidifying agent is selected from the group consisting of tartaric acid and citric acid.

5. The oral dosage formulation of claim 4, wherein the acidifying agent is tartaric acid.

6. The oral dosage formulation of claim 1, further comprising a binder.

7. The oral dosage formulation of claim 6, wherein the binder is present in an amount of from about 0.5 to about 10.0 weight percent.

8. The oral dosage formulation of claim 7, wherein the binder is present in an amount of from about 1.0 to about 5.0 weight percent.

9. The oral dosage formulation of claim 6, wherein the binder comprises sodium alginate.

10. The oral dosage formulation of claim 1, wherein the ibrutinib is Form I ibrutinib.

11. The oral dosage formulation of claim 1, wherein the oral dosage form is a capsule.

12. The oral dosage formulation of claim 1, wherein the oral dosage form releases about 90% or more of the ibrutinib within about 45 minutes.

13. A method of treating a cancer by administering to a patient in need thereof the oral dosage formulation of claim 1.

14. A method of treating a graft versus host disease by administering to a patient in need thereof the oral dosage formulation of claim 1.

15. A solid oral dosage formulation comprising ibrutinib having a particle size $d_{90}$ of from about 75 to about 105 microns, an acidifying agent present in an amount of about 1.0 to about 5.0 weight percent, a binder present in an amount of from about 1.0 to about 10 weight percent, and an ionic surfactant present in an amount of from about 0.1 to about 2 weight percent, wherein the oral dosage formulation releases about 70% or more of the ibrutinib within about 45 minutes when measured in either 900 mL of 3.0% w/v Polysorbate 20 in 50 mM phosphate buffer, pH 6.8, paddles at 75 rpm or 900 mL of 0.1 N HCl, paddles at 50 rpm.

16. The oral dosage formulation of claim 15, wherein the acidifying agent is selected from tartaric acid and citric acid, and wherein the binder is sodium alginate, and wherein the surfactant is sodium lauryl sulfate.

17. The oral dosage formulation of claim 15, further comprising one or more of a lubricant, a filler, and/or a disintegrant.

18. A solid oral dosage formulation consisting essentially of ibrutinib, an acidifying agent, a binder, an ionic surfactant, a lubricant, a filler, and a disintegrant, wherein the ibrutinib has a particle size $d_{90}$ of from about 75 to about 105 microns, and wherein the dosage formulation releases about 70% or more of the ibrutinib within about 45 minutes when tested in either 900 mL of 3.0% w/v Polysorbate 20 in 50 mM phosphate buffer, pH 6.8, paddles at 75 rpm or 900 mL of 0.1 N HCl, paddles at 50 rpm.

19. The oral dosage formulation of claim 18, wherein the acidifying agent is present in an amount of from about 1.0 weight percent to about 3.0 weight percent.

20. The oral dosage formulation of claim 18, consisting essentially of ibrutinib, tartaric acid or citric acid, sodium alginate, sodium lauryl sulfate, magnesium stearate, a microcrystalline cellulose and croscarmellose sodium.

21. The oral dosage formulation of claim 20, wherein the tartaric acid or citric acid is present in an amount of from about 1.0 to about 3.0 weight percent.

22. The oral dosage formulation of claim 20, wherein the sodium alginate is present in an amount of from about 1.0 to about 5.0 weight percent.

23. The oral dosage form of claim 2, wherein the oral dosage formulation releases about 90% or more of the ibrutinib within about 45 minutes.

24. The oral dosage form of claim 20, wherein the oral dosage formulation releases about 90% or more of the ibrutinib within about 45 minutes.

25. The oral dosage formulation of claim 18 consisting of ibrutinib, an acidifying agent, a binder, a non-ionic surfactant, a lubricant, a filler, and a disintegrant.

26. The oral dosage form of claim 25, wherein the oral dosage formulation releases about 90% or more of the ibrutinib within about 45 minutes.

27. The oral dosage formulation of claim 25, consisting of ibrutinib, tartaric acid or citric acid, sodium alginate, sodium lauryl sulfate, magnesium stearate, a microcrystalline cellulose and croscarmellose sodium.

28. The oral dosage form of claim 27, wherein the oral dosage formulation releases about 90% or more of the ibrutinib within about 45 minutes.

* * * * *